(12) United States Patent
Ashtekar et al.

(10) Patent No.: US 7,541,417 B2
(45) Date of Patent: Jun. 2, 2009

(54) PROCESS FOR THE PURIFICATION OF DIHYDRIC PHENOLS

(75) Inventors: Sunil Ashtekar, Karnataka (IN); Mahesh Malusare, Karnataka (IN); Gurram Kishan, Karnataka (IN); Pushpa Narayanan, Karnataka (IN); Ramanarayanan GV, Karnataka (IN); Arun Dixit, Karnataka (IN); Pradeep Nadkarni, Karnataka (IN); Jan Plen Lens, Breda (NL)

(73) Assignee: SABIC Innovative Plastics IP B.V., Bergen op Zoom (NL)

( * ) Notice: Subject to any disclaimer, the term of this patent is extended or adjusted under 35 U.S.C. 154(b) by 278 days.

(21) Appl. No.: 11/277,957

(22) Filed: Mar. 30, 2006

(65) Prior Publication Data

US 2007/0232775 A1    Oct. 4, 2007

(51) Int. Cl.
*C08G 64/00* (2006.01)
*C08G 63/00* (2006.01)

(52) U.S. Cl. ............ 528/196; 528/176; 528/190; 528/193; 562/485; 562/486; 562/600; 568/637; 568/749; 568/750

(58) Field of Classification Search .......... 528/176, 528/190, 193, 196; 562/485, 486, 600; 568/637, 568/749, 750
See application file for complete search history.

(56) References Cited

U.S. PATENT DOCUMENTS

| | | |
|---|---|---|
| 3,351,669 A | 11/1967 | Anderson et al. |
| 5,436,359 A | 7/1995 | Masuya et al. |
| 5,675,021 A | 10/1997 | Eggeman et al. |
| 5,811,538 A | 9/1998 | Riley et al. |
| 6,417,346 B1 | 7/2002 | Salome et al. |
| 6,525,226 B2 | 2/2003 | Choudhary et al. |
| 6,548,722 B1 | 4/2003 | Choudhary et al. |
| 6,554,967 B1 | 4/2003 | Tanaka et al. |
| 6,716,510 B2 * | 4/2004 | Tomioka et al. ............ 428/64.7 |
| 6,962,967 B2 | 11/2005 | Peters et al. |
| 2003/0018219 A1 | 1/2003 | Choudhary et al. |
| 2005/0222380 A1 | 10/2005 | Peters et al. |
| 2007/0232774 A1 * | 10/2007 | Xiu et al. ............... 528/86 |

FOREIGN PATENT DOCUMENTS

| | | |
|---|---|---|
| GB | 811519 A | 4/1959 |
| GB | 1357280 A | 6/1974 |
| GB | 1426769 A | 3/1976 |
| JP | 2000159715 A2 | 6/2000 |
| JP | 2004016897 A2 | 1/2004 |
| JP | 2005053845 A2 | 3/2005 |
| WO | WO 03011865 A1 | 2/2003 |
| WO | WO 2004096747 A1 | 11/2004 |
| WO | WO 2005007667 A1 | 1/2005 |
| WO | WO 2005035468 A1 | 4/2005 |
| WO | WO 2005108400 A1 | 11/2005 |

OTHER PUBLICATIONS

Sci-Tech Encyclopedia McGraw-Hill Encyclopedia of Science and Technology, 5th edition, published by The McGraw-Hill Companies, Inc. 2008.*
PCT International Search Report for International Application No. PCT/US2007/004302, filed Feb. 16, 2007.

* cited by examiner

*Primary Examiner*—Terressa M Boykin

(57) ABSTRACT

A process comprising the steps of dissolving a dihydric phenol in a solvent to form a solution A, contacting the solution A with an adsorbent material selected from the group consisting of metal oxides, modified metal oxides, activated carbons, and clays, filtering the adsorbent material to form a solution B, adding an anti-solvent to the solution B to form a solution C, and distilling the solution C, wherein the dihydric phenol is represented by Formula (I):

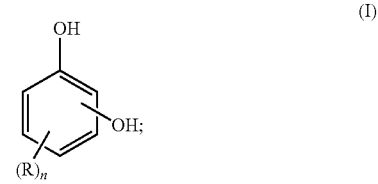

wherein R is a hydrogen atom or an aliphatic functionality having 1 to 6 carbon atoms and n is an integer having a value of 1 to 4.

22 Claims, No Drawings

PROCESS FOR THE PURIFICATION OF DIHYDRIC PHENOLS

BACKGROUND

This disclosure generally relates to a method for the purification of dihydric phenols. More particularly the disclosure relates to a method for the purification of methyl hydroquinone.

The present method of preparing dihydric phenols involves oxidation of the corresponding aromatic amines to benzoquinones followed by the reduction of the benzoquinones to hydroquinones. For example, the commercial process for the preparation of methyl hydroquinone employs o-toluidine as the raw material. The acid sulfate of o-toluidine is prepared by sulfuric acid treatment and is oxidized with manganese dioxide and sulfuric acid at lower temperatures of about 5° C. to about 8° C. The methyl benzoquinone formed is then steam distilled and reduced in the presence of zinc and/or iron and acid to form methyl hydroquinone. The isolated methyl hydroquinone has a typical purity of 99 percent and typically contains about 30 parts per million (ppm) to about 50 ppm of metals like iron, manganese, sodium, zinc, calcium and others as impurities. One of the main uses of methyl hydroquinone is in the preparation of co-polymers having good chemical resistance properties.

Methyl hydroquinone can be used in the preparation of co-polymers such as polycarbonates and polyesters. The presence of the metal residues in methyl hydroquinone in ppm levels considerably affects the properties of the co-polymer, such as for example, a reduced molecular weight buildup, reduced transparency, and an increase in color. This is true especially for dihydroxy based co-polymers and especially BPA containing PC. It is believed that metal ions present even in ppm levels, especially the transition metals like iron, can give rise to color formation during polymerization and further processing at high temperatures by forming colored metal complexes as by-products. Further, side reactions such as Fries rearrangement, which is known to be catalyzed by metals, can also occur during the polymerization.

Hence there is a need for a better purification technique that will help to reduce the metal ion concentration in the dihydric phenol to an amount such that the residual metal ion or ions will not interfere with the properties of the co-polymer prepared using the purified dihydric phenol.

BRIEF SUMMARY

Disclosed herein is a process for the purification of dihydric phenols. In one embodiment, the process comprises the steps of dissolving a dihydric phenol in a solvent to form a solution A; contacting the solution A with an adsorbent material selected from the group consisting of metal oxides, modified metal oxides, activated carbons, and clays; filtering the adsorbent material to form a solution B; adding an anti-solvent to the solution B to form a solution C; and distilling the solution C; wherein the dihydric phenol is represented by Formula (I):

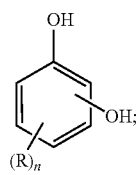

(I)

wherein R is a hydrogen atom or an aliphatic functionality having 1 to 6 carbon atoms and n is an integer having a value of 1 to 4.

In another embodiment, the process comprises the steps of dissolving the dihydric phenol in a mixture of a solvent and an anti-solvent to form a solution A; contacting the solution A with an adsorbent material selected from the group consisting of metal oxides, modified metal oxides, activated carbons, and clays; filtering the adsorbent material to form a solution B; and distilling the solution B; wherein the dihydric phenol is represented by Formula (I):

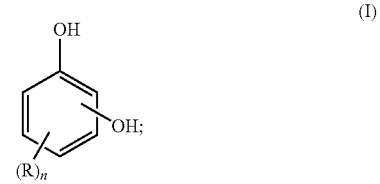

(I)

wherein R is a hydrogen atom or an aliphatic functionality having 1 to 6 carbon atoms and n is an integer having a value of 1 to 4.

The disclosure may be understood more readily by reference to the following detailed description of the various features of the disclosure and the examples included therein.

DETAILED DESCRIPTION

Disclosed herein is a process for the purification of dihydric phenols. Dihydric phenols are generally useful as monomers or co-monomers in the preparation of polymers. Some dihydric phenols, for example methyl hydroquinone, are key monomers for preparing polycarbonates (PC) that are used in specialty applications, such as for example in packaging of cosmetic, perfume, or biochemical applications.

The singular forms "a", "an" and "the" include plural referents unless the context clearly dictates otherwise. All ranges disclosed herein are inclusive of the recited endpoint(s) and independently combinable (for example ranges of "from about 2 grams to about 10 grams" is inclusive of the endpoints and all the intermediate values of the ranges of 2 grams to about 10 grams).

The modifier "about" used in connection with a quantity is inclusive of the stated value and has the meaning dictated by the context (for example, includes the degree of error associated with measurement of the particular quantity).

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

As used herein the term "aliphatic functionality" refers to an organic functionality having at least one carbon, a valence of at least one consisting of a linear or branched array of atoms that is not cyclic. For example, aliphatic functionalities include, but are not limited to, methyl, ethyl, propyl, isopropyl, butyl, isobutyl, pentyl and isopentyl groups.

Disclosed herein is a process for the purification of dihydric phenols. The purification process results in a reduction in the concentration of iron (Fe), zinc (Zn), sodium (Na), calcium (Ca), manganese (Mn), and other metal ions that may be present in the unpurified dihydric phenols from ppm levels to parts per billion (ppb) levels. One process for the purification of a dihydric phenol of Formula (I) comprises the steps of dissolving the dihydric phenol in a solvent to form a solution A; contacting the solution A with an adsorbent material selected from the group consisting of metal oxides, modified metal oxides, activated carbons, and clays; filtering the adsorbent material to form a solution B; adding an anti-solvent to the solution B to form a solution C; and distilling the solution C.

In another embodiment, a process for the purification of a dihydric phenol of Formula (I) comprises dissolving the dihydric phenol in a mixture of a solvent and an anti-solvent to form a solution A; contacting the solution A with an adsorbent material selected from the group consisting of metal oxides, modified metal oxides, activated carbons, and clays; filtering the adsorbent material to form a solution B; and distilling the solution B.

Non-limiting examples of the dihydric phenols of Formula (I) that can be purified using the processes disclosed herein include, but are not limited to, hydroquinone, resorcinol, catechol, 2-methyl-1,4-hydroquinone, 2,5-dimethyl-1,4-hydroquinone, 2-ethyl-1,4-hydroquinone, 2,5-diethyl-1,4-hydroquinone, 2-tertiarybutyl-1,4-hydroquinone, 2,3,5-trimethyl-1,4-hydroquinone, 2-isopropyl-1,4-hydroquinone, and 2,5-diisopropyl-1,4-hydroquinone. Mixtures of two or more of the foregoing dihydric phenols can also be purified.

Suitable solvents that can be employed for dissolving the dihydric phenol comprise water, ketones having 3 to 10 carbons, alcohols having 1 to 12 carbons, esters having 4 to 10 carbons or mixtures of the foregoing solvents. Specific, non-limiting examples of suitable solvents include acetone, methyl ethyl ketone, methyl isobutyl ketone, methyl butyl ketone, methyl propyl ketone, methyl alcohol, ethyl alcohol, isopropyl alcohol, butyl alcohol, isobutyl alcohol, isopentyl alcohol, n-pentyl alcohol, n-hexyl alcohol, ethyl acetate, butyl acetate, and a mixture of one or more of the foregoing solvents. A mixture having a suitable amount of water and one or more of the solvents listed above can also be used to dissolve the dihydric phenol. In one embodiment the solvent used is acetone.

The amount of the solvent used in the purification can be from about 0.5 grams to about 10 grams, per gram of the dihydric phenol. Within this range the amount may be greater than or equal to about 1 grams, or more specifically, greater than or equal to about 3 grams, per gram of the dihydric phenol. Also within this range the amount may be less than or equal to about 7 grams, or more specifically less than or equal to about 5 grams, per gram of the dihydric phenol.

Suitable anti-solvents used in the purification of the dihydric phenol include hydrocarbon solvents having 6 to 20 carbons. Examples of suitable anti-solvents include, but are not limited to, hexane, petroleum ether, toluene, xylene, and a mixture of one or more of the foregoing anti-solvents. In one embodiment, the anti-solvent used is toluene.

The amount of the anti-solvent used in the purification can be from about 2 grams to about 40 grams per gram of the dihydric phenol. Within this range the amount may be greater than or equal to about 3 grams, or more specifically, greater than or equal to about 10 grams, per gram of the dihydric phenol. Also within this range the amount may be less than or equal to about 25 grams, or more specifically less than or equal to about 20 grams, per gram of the dihydric phenol. It is to be noted that the solvent used in the purification process must have a lower boiling point than the boiling point of the anti-solvent. Specific non-limiting examples of solvent and anti-solvent combinations include, acetone and toluene; methyl ethyl ketone and toluene; methyl isobutyl ketone and toluene; and methyl isobutyl ketone and petroleum ether.

In one embodiment, where a mixture of a solvent and an anti-solvent is employed to dissolve the dihydric phenol, the combined amount of the solvent and the anti-solvent used in the purification can be about 2.5 grams to about 50 grams, per gram of the dihydric phenol. Within this range the amount may be greater than or equal to about 4 grams, or more specifically, greater than or equal to about 13 grams, per gram of the dihydric phenol. Also within this range the amount may be less than or equal to about 32 grams, or more specifically, less than or equal to about 25 grams, per gram of the dihydric phenol. Typically the amount of anti-solvent used is about 4 times the amount of the solvent used in the process. It is to be noted that to ensure complete dissolution of the dihydric phenol in the solvent or in the combination of the solvent and the anti-solvent, the dissolution step may be carried out at a temperature of about 25° C. to about 100° C. Within this range, the temperature may be greater than or equal to about 40° C., or more specifically, greater than or equal to about 50° C. Also within this range, the temperature may be less than or equal to about 90° C., or more specifically, less than or equal to about 80° C.

Suitable adsorbent materials that can be used are selected from the group consisting of metal oxides, modified metal oxides, activated carbons, and clays.

Specific examples of suitable metal oxides include, but are not limited to, silica ($SiO_2$), zirconia ($ZrO_2$), magnesia (MgO), and alumina ($Al_2O_3$). Commercially available silica of different mesh sizes can be used. In certain embodiments, silica having a mesh size ranging from about 60 to about 600 mesh size may be employed as the adsorbent material. In certain other embodiments, the mesh size of silica used can be from about 60 to about 120 size mesh, or from about 300 to 500 mesh size.

Specific examples of the modified metal oxides include, but are not limited to, water-washed silica and acid-washed silica. Without being bound by theory, it is believed that when silica available from commercial sources is washed with water or with an acid, the metals that are loosely bound to the silica are washed away, thereby avoiding the leaching of metals form the silica to the dihydric phenol and thereby increasing the adsorption capacity of silica. Generally, a mineral acid, such as for example, aqueous hydrochloric acid of varying normality can be used for washing the silica. Other suitable acids that are generally known to one of skill in the art can also be used.

Suitable examples of the activated carbon include, but are not limited to, the NORIT series of activated carbon available from Norit Corporation, CARBOCHEM® grades of activated carbon available from Carbochem and the activated carbons commercially available from E. Merck Company. In one embodiment, the activated carbon is selected from the NORIT series of activated carbon.

Suitable examples of clays include, but are not limited to, apophyllite, bannisterite, carletonite, cavansite, chrysocolla, delhayelite, elpidite, fedorite, franklinfurnaceite, gonyerite, gyrolite, leucosphenite, minehillite, nordite, pentagonite, petalite, prehnite, rhodesite, sanbornite, baileychlore, chamosite, cookeite, nimite, pennantite, penninite, sudoite, glauconite, illite, kaolinite, montmorillonite, palygorskite, pyrophyllite, sauconite, vermiculite, biotite, lepidolite, muscovite, paragonite, phlogopite, zinnwaldite, Englehardt clay, and hydrotalcite. In one embodiment, the clay is Englehardt clay, montmorillonite or hydrotalcite.

In certain embodiments, the amount of the adsorbent material used for purifying the dihydric phenols can be about 2 percent by weight to about 30 percent by weight, relative to an amount of the dihydric phenol. Within this range the amount may be greater than or equal to about 2.5 percent by weight, or more specifically, greater than or equal to about 5 percent by weight, relative to an amount of the dihydric phenol. Also within this range the amount may be less than or equal to about 20 percent by weight, or more specifically less than or equal to about 15 percent by weight, relative to an amount of the dihydric phenol.

As previously described, the solution A obtained is contacted with the adsorbent material to effect purification of the dihydric phenol. This step of contacting the solution A with the adsorbent is carried out at a temperature of from about 25° C. to about 120° C. Within this range, the temperature may be greater than or equal to about 40° C., or more specifically, greater than or equal to about 50° C. Also within this range, the temperature may be less than or equal to about 110° C., or more specifically, less than or equal to about 80° C. The time taken for the purification of the dihydric phenol can be about 0.5 hours to about 3 hours. Within this range the time may be greater than or equal to about 1 hour, or more specifically, greater than or equal to about 1.25 hours. Also within this range the time may be less than or equal to about 2.5 hours, or more specifically, less than or equal to about 2 hours.

Typically, the purified dihydric phenol is isolated by distilling the solution C. In one embodiment, isolation of the purified dihydric phenol can be achieved by partially distilling the lower boiling solvent from the solution C. The partial distillation of the solvent results in the precipitation of the purified dihydric phenol, and the remainder of the solvent present in the solution C helps to keep the color forming impurities in solution. The amount of solvent distilled is about 10 percent by weight to about 80 percent by weight, relative to the amount of the solvent employed for the dissolution of the impure dihydric phenol to form the solution A. Within this range, the amount of the solvent may be greater than or equal to about 30 percent by weight, or more specifically, greater than or equal to about 40 percent by weight, relative to the amount of the solvent used to form the solution A. Also within this range, the amount of the solvent may be less than or equal to about 70 percent by weight, or more specifically, less than or equal to about 50 percent by weight, relative to the amount of the solvent used to form the solution A. Alternately, when the dihydric phenol is dissolved in a mixture of the solvent and the anti-solvent, isolation of the purified dihydric phenol can be achieved by partially distilling the solvent from the solution B. The purification of the dihydric phenol can be carried out in a batch mode, continuous mode or in a semi-continuous mode as known to a person skilled in the art.

The reduction in metal ion concentration in the dihydric phenols of Formula (I) provides the purified dihydric phenol. In one embodiment, the purified dihydric phenol is characterized by an APHA (American Public Health Association) value of less than or equal to 40.

As previously discussed, one of the end uses of the purified dihydric phenols is in the preparation of polymers and co-polymers, for example, polycarbonates. The polymers and co-polymers comprise structural units derived from the dihydric phenols having Formula (I), where the structural units are represented by Formula (II):

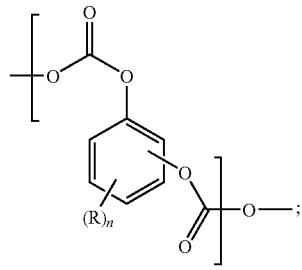

wherein R and n are as described previously. Suitable methods for preparation of polycarbonates include, but are not limited to, interfacial polymerization and melt transesterification polymerization methods. In the interfacial polymerization method, the purified dihydric phenols of Formula (I) are reacted with phosgene to provide the polycarbonates. In melt-transesterification polymerization, the purified dihydric phenols are either homopolymerized, or copolymerized with one or more bisphenols other than the dihydric phenols of Formula (I) in the presence of carbonate precursors, such as for example, diphenyl carbonate or bismethylsalicyl carbonate (bMSC). A catalyst is generally used to effect the transesterification reaction. Suitable examples of the catalysts include quaternary phosphonium salts, tetraalkylammonium salts, sodium hydroxide, or combinations of sodium hydroxide with the quaternary phosphonium salts or the tetraalkylammonium salts. The polymers or co-polymers prepared using the purified dihydric phenol show increased molecular weight build up, increased transparency, and improved color, that is, a lower yellowness index (YI). The color improvement in the purified dihydric phenol can be measured in terms of the APHA value. The color improvement in the polymer prepared using the purified dihydric phenols can be measured in terms of YI.

The polymer or co-polymer prepared using the purified dihydric phenol can be used in various polymer compositions. The compositions may further optionally include various additives ordinarily incorporated in resin compositions of this type. Such additives may include antioxidants, heat stabilizers, flame retardants, UV stabilizers, anti-static agents (tetraalkylammonium benzene sulfonate salts, tetraalkylphosphonium benzene sulfonate salts, and the like), mold releasing agents (pentaerythritol tetrastearate, glycerol monostearate, and the like), and the like, and combinations comprising the foregoing. For example, the polymer composition can comprise a heat stabilizer from about 0.01 weight percent to about 0.1 weight percent; an antistatic agent from about 0.01 weight percent to about 1 weight percent; and/or a mold releasing agent from about 0.1 weight percent to about 1 weight percent, each based upon the total weight of the polymer.

The polymer compositions may be used for any application where desirable material properties, such as good physical properties, low color, and high transparency are required. In certain embodiments, the polymers may be used for packaging applications (especially for packaging drugs, cosmetics, perfumes, and biochemical materials), automotive parts, telecommunication accessories (for example, cell phone covers), computers and consumer electronics, construction materials, medical devices, eyewear products, secure documents including passports and ID cards, credit cards, films and sheets (including those used in display applications), and others.

A further understanding of the techniques described above can be obtained by reference to certain specific examples that are provided herein for purposes of illustration only and are not intended to be limiting.

EXAMPLES

The following examples illustrate processes by which dihydric phenols can be purified by using specific adsorbent materials, thereby leading to a purified dihydric phenol having a reduced APHA value. Further, the examples illustrate that the purified dihydric phenols can be used as monomers for making polycarbonates having a reduced YI.

Methyl hydroquinone (MeHQ) used in the examples was obtained from commercial sources, such as, for example, Hunan, a supplier from China. The starting sample was about 99 percent pure when analyzed using liquid chromatography, based on weight percent. The starting sample of MeHQ is hereinafter referred to as "raw MeHQ". The metal ion concentrations in the raw MeHQ sample are provided in parts per billion (ppb) in Table 1 below.

TABLE 1

| Raw MeHQ | | | | | |
|---|---|---|---|---|---|
| Fe | Na | Zn | Mn | Ca | APHA |
| 21400 | 25500 | 58600 | 13800 | 1410 | 139 |

APHA values were measured using a Macbeth Spectrophotometer using a 10 weight percent (weight by volume) solution of the purified dihydric phenol in acetonitrile (ACN).

Inductively Coupled Plasma (ICP) Atomic Emission Spectrometer was used to measure the concentration of, sodium, potassium, calcium, iron, zinc, nickel, manganese, chromium and aluminum in ppm and ppb levels. The samples were analyzed using Spectro Ciros equipped with an ultrasonic nebulizer UT5000AT+. The sample used for analysis was prepared as follows. 10 grams (g) of a sample of MeHQ (purified or unpurified MeHQ) was weighed in a platinum crucible and 2 milliliters (ml) of 50 percent aqueous sulphuric acid was added. The platinum crucible was then heated to about 650° C. to char the sample. The residue obtained at the end was cooled to room temperature and treated with 2 ml of hydrochloric acid to form a solution. The solution was then transferred to a polypropylene container, diluted to 50 ml with deionized water and sprayed into the ICP-AES for estimation of metal content.

The general procedure followed for purification is provided below. Raw MeHQ (50 g), acetone (38 ml) and toluene (200 ml) were charged into a one-liter round bottom flask equipped with a condenser and a nitrogen blanket. The flask was then heated in an oil bath at 90° C. for about 30 to 45 minutes until all the raw MeHQ was dissolved. After complete dissolution of the raw MeHQ, the adsorbent was added, and the resultant mixture was stirred at 90° C. at about 200 revolutions per minute for about 2 hours. The mixture was then filtered, and the filtrate was concentrated at 70° C. under a reduced pressure of 300 millibar. The pressure was slowly reduced to 175 millibar resulting in the precipitation of purified MeHQ. The mixture was then maintained at 5° C. for about 24 hours, and filtered and washed with 100 milliliters of toluene. The purified MeHQ was then dried, and the sample analyzed for ICP trace metal analysis, HPLC purity and APHA value. The isolated yield of the purified MeHQ was 90 percent of the theoretical yield. The general procedure described hereinabove was used with specific adsorbents as described below.

Examples 1-2

These examples provide a method for the purification of methyl hydroquinone using activated carbon as the adsorbent.

The procedure described above was used for purifying raw MeHQ using activated carbon obtained from Norit corporation. The solvent systems used were a mixture of methyl isobutyl ketone (MIBK; 150 milliliters) and toluene (150 milliliters) in Example 1; and a mixture of MIBK (150 milliliters) and petroleum ether (150 milliliters) in Example 2. Different amounts (weight percents) of activated carbon were used in Examples 1 and 2. Results of metal ion concentration (expressed in ppb levels) in the purified MeHQ are shown in Table 2 below.

TABLE 2

| Example No. | Activated carbon weight percent based on relative amount of MeHQ | Solvent | Fe | Na | Zn | Mn | Ca | APHA |
|---|---|---|---|---|---|---|---|---|
| 1 | 5 | MIBK-Toluene | 620 | 58000 | 310 | 70 | 1110 | 25 |
| 2 | 10 | MIBK-Petroleum Ether | 1110 | 2410 | 190 | 50 | 3400 | 34 |

Example 3-9

These Examples provide a method for the purification of MeHQ using silica as the adsorbent.

The procedure used in Examples 3-6 for purifying raw MeHQ using silica is as described above in the general procedure used for purification. The procedure used in Examples 7-9 includes dissolution of MeHQ in toluene at reflux temperature and stirring with silica at the same temperature for 1 hour. The solution is then cooled to 80° C. and acetone is added. The silica is then filtered and the filtrate concentrated to give MeHQ. The different amounts of silica used in the solvent and the mesh size of silica used are included in the Table 3 below. Results of metal ion concentration (expressed in ppb levels) in MeHQ after purification are tabulated in Table 3 below.

TABLE 3

| Example No. | Silica weight percent based on a relative amount of raw MeHQ (mesh size of particles) | Temperature (° C.) | Solvent | Fe | Na | Zn | Mn | Ca | APHA |
|---|---|---|---|---|---|---|---|---|---|
| 3 | 5 (300-500 mesh) | RT | Acetone | 300 | 1120 | <20 | <20 | 920 | 32 |
| 4 | 10 (300-500 mesh) | 60 | Acetone + toluene | 250 | 1820 | 40 | 30 | 1050 | 31 |
| 5 | 10 (60-120 mesh) | 80 | Acetone + toluene | 270 | 260 | 40 | 110 | 420 | 24 |
| 6 | 10 (60-120 mesh) | 80 | Acetone + toluene | 390 | 310 | <10 | 180 | 280 | 40 |
| 7 | 6 (60-120 mesh) | 110 | Toluene followed by acetone | 180 | 113 | 130 | 50 | 740 | 22 |
| 8 | 6 (60-120 mesh) | 110 | Toluene followed by acetone | 80 | 410 | 250 | 80 | 1900 | 14 |
| 9 | 6 (60-120 mesh) | 110 | Toluene followed by acetone | 90 | <10 | 140 | 50 | <10 | 10 |

Examples 10-13

These Examples provide a method for the purification of MeHQ using water washed silica and acid washed silica, i.e., modified silica, as the adsorbent material.

Preparation of water washed silica: Silica (100 g) was refluxed with 500 ml of water for about 30 minutes, filtered and dried in an oven at 120° C. to obtain water washed silica.

Preparation of acid washed silica: Silica (100 g) was refluxed with 500 ml of 1 Normal hydrochloric acid for about 30 minutes, filtered and washed with water until the pH of the filtrate was neutral. The silica was then dried in an oven at 120° C. to obtain acid washed silica.

Table 4 shows the difference in metal ion concentration (expressed in ppb levels) in commercial silica and silica subjected to water or acid wash.

TABLE 4

| Source | Fe | Na | Zn | Mn | Ca |
|---|---|---|---|---|---|
| Starting material for water wash | 24700 | 442900 | 1900 | 700 | 273700 |
| Water washed Silica | 8500 | 342400 | <10 | 400 | 148100 |
| Acid washed silica | 10,400 | 8800 | 980 | <10 | 51400 |

The procedure used for purifying raw MeHQ using modified silica is as described above in the general procedure used for purification. The amount of water washed silica or acid washed silica used was 10 weight percent based on the amount of raw MeHQ, in an acetone/toluene (15/85 volume by volume) solvent system. The results of metal ion concentration (expressed in ppb levels) in MeHQ after purification are tabulated in Table 5 below.

TABLE 5

| Example No. | Modified silica | Fe | Na | Zn | Mn | Ca | APHA |
|---|---|---|---|---|---|---|---|
| 10 | Water washed | 550 | 200 | 190 | 30 | 220 | 18 |
| 11 | Water washed | 320 | 170 | 40 | <20 | 240 | 18 |

TABLE 5-continued

| Example No. | Modified silica | Fe | Na | Zn | Mn | Ca | APHA |
|---|---|---|---|---|---|---|---|
| 12 | Water washed | 260 | 180 | 550 | <20 | 370 | 20 |
| 13 | Acid washed | 139 | 179 | 35 | <20 | 443 | 26 |

Example 14-16

These Examples provide a method for the purification of MeHQ using alumina as the adsorbent material.

The procedure used for purifying raw MeHQ using alumina is as described above in the general procedure used for purification. The amount of alumina employed was 10 weight percent based on the amount of raw MeHQ, in an acetone/toluene (50/50 volume by volume) solvent system. Results of metal ion concentration (expressed in ppb levels) in MeHQ after purification are tabulated in Table 6 below.

TABLE 6

| Example No. | Fe | Na | Zn | Mn | Ca | APHA |
|---|---|---|---|---|---|---|
| 14 | 200 | 130 | 130 | <10 | 280 | 11 |
| 15 | 260 | 870 | 130 | <20 | 870 | 7 |
| 16 | 730 | 570 | 550 | 30 | 570 | 10 |

Example 17-18

These Examples provide a method for the purification of MeHQ using clays are the adsorbent material.

The procedure used for purifying the raw MeHQ using an Engelhardt clay (commercially available from Engelhardt Corporation) adsorbent material is as described above. The amount of clay employed was 10 weight percent in an acetone/toluene (50/50 volume by volume) solvent system. Results of metal ion concentration (expressed in ppb levels) in MeHQ after purification are tabulated in Table 7 below.

TABLE 7

| Example No. | Adsorbent | Fe | Na | Zn | Mn | Ca | APHA |
|---|---|---|---|---|---|---|---|
| 17 | Engelhardt F-20 | 270 | 300 | 290 | <20 | 690 | 12 |
| 18 | Engelhardt F-24 | 480 | 640 | 300 | 30 | 10,300 | 33 |

Comparative Examples 1 to 4 (CE-1 to CE-4)

These Examples provide a method for the purification of MeHQ using cationic ion exchange resin as the adsorbent.

The procedure used for purifying raw MeHQ using cationic ion exchange resin is as described above in the general procedure used for purification. The amount of ion exchange resin employed was 10 weight percent based on the amount of raw MeHQ, in an acetone/toluene (50/50 volume by volume) solvent system or of a MIBK/toluene (50/50 volume by volume) solvent system. Results of metal ion concentration in MeHQ after purification are tabulated in Table 8 below. Resins tried for purification were Bayer 2 percent polystyrene divinylbenzene cross-linked resin (K1131), chelating resin CH-90, T-42 MPH (which is a high capacity macroporous cation exchange resin) as listed in Table 8 below.

TABLE 8

| Example No. | Adsorbent | Solvent | Fe | Na | Zn | Mn | Ca | APHA |
|---|---|---|---|---|---|---|---|---|
| CE-1 | K1131 | Acetone + toluene | 3500 | 3700 | 8600 | 1500 | 1700 | NA |
| CE-2 | CH-90 | MIBK + toluene | 5280 | 7500 | 19400 | 3200 | 980 | NA |
| CE-3 | T-42 | Acetone + toluene | 3900 | 3600 | 7200 | 1500 | 650 | 81 |
| CE-4 | T-42 | MIBK + toluene | 2200 | 4220 | 1270 | 300 | 1400 | 78 |

Based on all the results provided above, it was found that some of the adsorbents used give better reduction in APHA value. For example, silica used in Examples 3-9, modified silica used in Examples 10-13 and alumina used in Examples 14-16 indicate that the APHA value are less than the APHA value obtained when cationic ion exchange resins is used as the adsorbent as indicated in Comparative Examples 3-4. This shows that not all the adsorbents used helped lower the metal ion concentration and thereby lower the APHA value to less than or equal to 40. Even among the different silica adsorbents used only some adsorbents were capable of providing the APHA value of less than or equal to 20.

Examples 19-20

These Examples provide a method for the preparation of a co-polymer from the purified MeHQ.

The purified MeHQ was used as a monomer in the polymerization process. The polymerization was carried out by following the process described below. Bisphenol A (8.51 g) and MeHQ (4.62 g), transesterification catalyst (sodium hydroxide (5.96 microgram) and tetramethyl ammonium hydroxide (177 microgram), bismethyl salicyl carbonate (bMSC; 25 g), were charged into a glass reactor tube to form a mixture. The mixture was then purged with nitrogen. The temperature in this system was varied between 180° C. and 295° C. and the pressure varied from 1 atmosphere to 0 millibar. Co-polymers of MeHQ with bisphenol A (50/50 mole percent) were prepared and the properties, such as molecular weight and yellowness index, were evaluated. The molecular weight (MW) of the co-polymer was determined by Gel Permeation Chromatography (GPC) on a Shimadzu system, using chloroform as solvent at 35° C. through a PLgel 5 micrometer (10E3Angstrom & 10E5Angstrom) column and housed with a UV-detector at 254 nanometer (nm) and compared relative to polystyrene standards. The dYI (difference in yellowness index) values included in Table 9 below, were measured using a Macbeth Spectrophotometer, from a 10 weight percent (weight by volume) solution of the co-polymer in chloroform. The dYI value is equal to (YI of a solution of co-polymer in chloroform minus YI of chloroform).

In Example 19 and Example 20, the samples used for polymerization were the purified MeHQ from Example 12 (where water washed silica was used as the adsorbent material) and Example 15 (where alumina was used as the adsorbent material), respectively. The 50:50 co-polymer with bisphenol A was clear and the molecular weight build up was in the range of 59000 to 71000 (molecular weight based on polystyrene standards—MWPS). The results are tabulated in Table 9 below.

Comparative Example 5 (CE-5)

In this Example a 50:50 co-polymer of MeHQ with bisphenol-A was prepared in a similar manner as described in Examples 19 and 20, except that the purified MeHQ was replaced with raw MeHQ. The results are tabulated in Table 9 below.

TABLE 9

| Example no. | MeHQ | MWPS | dYI |
|---|---|---|---|
| 19 | Purified - Example 12 | 71000 | 2.259 |
| 20 | Purified - Example 14 | 68000 | 3.329 |
| CE-5 | Raw MeHQ | 39000 | 4.437 |

The above results show that the polymers prepared using the purified MeHQ, prepared as described above, have a higher molecular weight and a lower yellowness index, as compared with the polymers prepared using the raw MeHQ.

While typical embodiments have been set forth for the purpose of illustration, the foregoing descriptions should not be deemed to be a limitation on the scope herein. Accordingly, various modifications, adaptations, and alternatives may occur to one skilled in the art without departing from the spirit and scope herein.

The invention claimed is:

1. A method for purifying a dihydric phenol, the method comprising:

dissolving a dihydric phenol having Formula (I)

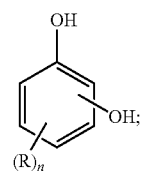

wherein R is a hydrogen atom or an aliphatic functionality having 1 to 6 carbon atoms; and n is an integer having a value of 1 to 4, in a solvent to form a solution A;

contacting the solution A with an adsorbent material selected from the group consisting of metal oxides, modified metal oxides, activated carbons, and clays, wherein the step of contacting is carried out at a temperature of about 25° C. to about 120° C;

filtering the adsorbent material to form a solution B;

adding an anti-solvent to the solution B to form a solution C, wherein the anti-solvent has a higher boiling point than the solvent; and distilling the solution C until about 10 to 80% of the original weight of the solvent is removed.

2. The method of claim 1, further comprising isolating a purified dihydric phenol.

3. A method for purifying a dihydric phenol, the method comprising:

dissolving a dihydric phenol having Formula (I)

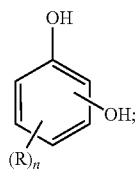

(I)

wherein R is a hydrogen atom or an aliphatic functionality having 1 to 6 carbon atoms; and n is an integer having a value of 1 to 4, in a mixture of a solvent and an anti-solvent to form a solution A, wherein the anti-solvent has a higher boiling point than the solvent;

contacting the solution A with an adsorbent material selected from the group consisting of metal oxides, modified metal oxides, activated carbons, and clays, wherein the step of contacting is carried out at a temperature of about 25° C. to about 120° C.;

filtering the adsorbent material to form a solution B; and distilling the solution B until about 10 to 80% of the original weight of the solvent is removed.

4. The method of claim 3, further comprising isolating the purified dihydric phenol.

5. The method of claim 1, wherein the dihydric phenol is 2-methyl-1,4-hydroquinone.

6. The method of claim 1, wherein the solvent comprises water, ketones having 3 to 10 carbons, alcohol having 1 to 12 carbons, esters having 4 to 10 carbons; or mixtures of one or more of the foregoing solvents.

7. The method of claim 1, wherein the solvent comprises acetone.

8. The method of claim 1, wherein the anti-solvent comprises hydrocarbon solvents having 6 to 20 carbons.

9. The method of claim 1, wherein the anti-solvent comprises toluene.

10. The method of claim 1, wherein the metal oxide comprises silica, zirconia, magnesia, or alumina.

11. The method of claim 1, wherein the modified metal oxide comprises water-washed silica or acid-washed silica.

12. The method of claim 1, wherein the clay comprises Engelhardt clay, montmorillonite or hydrotalcite.

13. The method of claim 1, wherein the adsorbent is present in an amount of about 2 percent by weight to about 30 percent by weight, relative to an amount of the dihydric phenol.

14. The method of claim 1, wherein the solvent is present in an amount of about 0.5 grams to about 10 grams, per gram of the dihydric phenol.

15. The method of claim 1, wherein the anti-solvent is present in an amount of about 2 grams to about 40 grams, per gram of the dihydric phenol.

16. The method of claim 3, wherein the adsorbent is present in an amount of about 2 percent by weight to about 30 percent by weight, relative to an amount of the dihydric phenol.

17. The method of claim 3, wherein the solvent is present in an amount of about 0.5 grams to about 10 grams, per gram of the dihydric phenol.

18. The method of claim 3, wherein the anti-solvent is present in an amount of about 2 grams to about 40 grams, per gram of the dihydric phenol.

19. A purified dihydric phenol prepared in accordance with the method of claim 1.

20. A polymer comprising structural units derived from the purified dihydric phenol of claim 19.

21. A purified dihydric phenol prepared in accordance with the method of claim 3.

22. A polymer comprising structural units derived from the purified dihydric phenol of claim 21.

\* \* \* \* \*